United States Patent [19]

Gramnäs

[11] Patent Number: 5,314,498

[45] Date of Patent: May 24, 1994

[54] ARTIFICIAL TOGGLE JOINT

[76] Inventor: Finn Gramnäs, Brantalid 18, 511 56 Kinna, Sweden

[21] Appl. No.: 941,041

[22] PCT Filed: Mar. 28, 1991

[86] PCT No.: PCT/SE91/00240

§ 371 Date: Oct. 1, 1992

§ 102(e) Date: Oct. 1, 1992

[87] PCT Pub. No.: WO91/15170

PCT Pub. Date: Oct. 17, 1991

[30] Foreign Application Priority Data

Apr. 2, 1990 [SE] Sweden ............................ 9001183

[51] Int. Cl.⁵ ............................................. A61F 2/64
[52] U.S. Cl. ........................................ 623/39; 623/44
[58] Field of Search .......................... 623/39, 43–44; 602/26; 403/54

[56] References Cited

U.S. PATENT DOCUMENTS

| | | | |
|---|---|---|---|
| 1,384,850 | 7/1921 | Pringle et al. | 623/43 |
| 1,847,823 | 3/1932 | Dresser | 623/43 X |
| 2,638,605 | 5/1953 | Johnson | 623/39 |
| 3,806,958 | 4/1974 | Gusev | 623/46 X |
| 4,064,569 | 12/1977 | Campbell | 623/43 |
| 4,215,442 | 8/1980 | Blatchford et al. | 623/39 |
| 4,961,416 | 10/1990 | Moore et al. | 602/26 |
| 5,201,776 | 4/1993 | Freeman | 623/46 |

FOREIGN PATENT DOCUMENTS 1109153  8/1984  U.S.S.R. .................. 623/44

Primary Examiner—Randall L. Green
Assistant Examiner—D. Willse
Attorney, Agent, or Firm—Gardner, Carton & Douglas

[57] ABSTRACT

An artificial knee-joint provided with linkage mechanisms, where a thigh part and a lower-leg part are mutually connected by tow base linkage arms, each of which is pivotally connected at respective ends with both the lower-leg part and the thigh part, wherein the pivotal attachment points of the lower-leg part are disposed in moveable attachment elements which mutually coact in a manner such that the knee-joint will automatically either adopt a substantially locked or a moveable position, depending on the direction of the load acting on the knee-joint. The first attachment element is pivotally connected to the two base linkage arms extending from the thigh part and has three pivot points, whereas the second attachment element has two pivot points. The back base linkage arm extending from the thigh part is pivotally connected to both attachment elements. The second attachment element is provided with a lock-stop device which limits movement of the attachment element. When walking, the movement of the attachment elements function to automatically lock the knee-joint and to terminate a walking step in a natural fashion.

8 Claims, 4 Drawing Sheets

ARTIFICIAL TOGGLE JOINT

The present invention relates to an artificial knee-joint according to the preamble of claim 1.

The gait of a thigh amputee is considerably different to that of the gait of a normal healthy person, due to the absence of important muscle groups. Because of the loss of the knee muscles, the amputee can no longer bend and then again actively stretch the knee-joint under load. In the case of earlier knee-joint prosthesis using various types of braking mechanisms, the prevention of leg collapse in the supporting phase, i.e. that period in which the foot is in contact with the ground or like surface, has only been achieved with a greater or lesser degree of security. Thus, differing degrees of supporting-phase stability have been achieved. The prosthetic leg is fitted to the amputee with the knee straight, and the knee then remains straight during a major part of the supporting phase. If the knee-joint mechanism is very stable, it is not possible to bend the knee until the supporting phase is terminated. This impossibility of bending the knee at the beginning and the end of the supporting phase means that the amputee must consume more energy when walking. The absence of calf muscles also means that the gait of the person wearing the prosthesis is more energy demanding than the gait of a normal person.

The present artificial knee-joint is constructed imitate the working mode of the human knee-joint, so that the amputee is able to walk with a natural gait. The knee-joint can be said to be a further development of the existing quadruple-point polycentric type of joint. By polycentric joint is meant here that the rotational centre has different positions at different knee-joint angles, i.e. there are several pivot centres. The human knee-joint is also polycentric. By polycentrical quadruple-jointed knee is meant a knee in which the thigh part and the lower-leg part are mutually joined by two linkage mechanisms, each being pivotally connected at its respective ends to the thigh part and the lower-leg part. This results in four pivot points. Quadruple joint mechanisms are now the most common joints available. However, in order to achieve high supporting-phase stability, it is necessary to supplement these mechanisms with some form of mechanical/hydraulic lock or brake device. The earlier known technical solutions generally cause the knee-joint to become highly complex and undesirably heavy.

Described and illustrated in U.S. Pat. No. 2,638,605 is a knee-joint which comprises linkage mechanisms in which locking is effected by means of a catch with the knee straight, this catch being released by means of a linkage mechanism which transmits movement of the toe-part to the knee-joint. In addition to being highly complicated, a serious drawback is that the knee-joint is apparently too heavy for practical use and results in an unnatural termination of a walking step.

The object of the present invention is to provide an improved polycentric knee-joint which has high supporting-phase stability, which is light in weight and with which locking of the knee-joint is effected automatically in a simple fashion as a result of the construction and design of the knee-joint, and also to eliminate the drawbacks encountered with earlier known techniques. These objects are achieved by means of the invention, in that the artificial knee-joint mentioned in the introduction is constructed in the manner defined in the characterizing clause of claim 1. The inventive knee-joint is a polycentric joint and includes a linkage mechanism consisting of a plurality of linkage arms of varying lengths which are mutually arranged to achieve high supporting-phase stability and a simple, automatic locking function. This locking function is effective solely in an extended position and solely when load is exerted on the heel. When the foot rolls over onto the forward part, as the wearer of the prosthesis walks, the locking mechanism is released automatically. This means that the locking mechanism will not prevent natural termination or completion of a walking step.

The invention will now be described in more detail with reference to the accompany drawings, in which FIG. 1 illustrates schematically a preferred embodiment of the invention;

Figure 1:
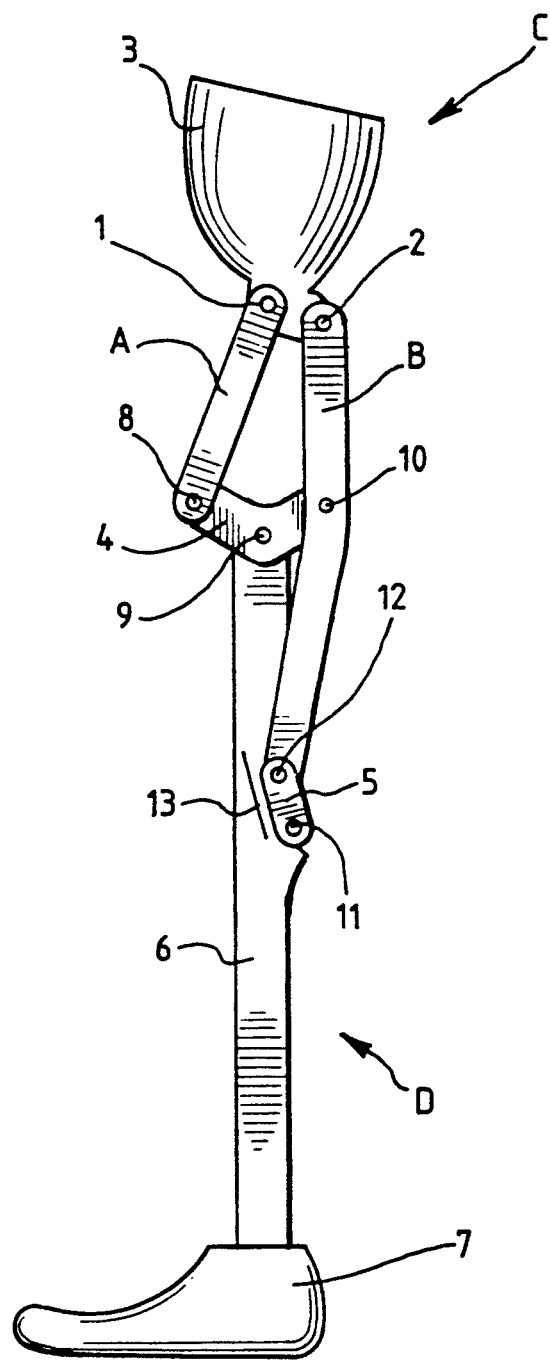

The knee-joint illustrated in FIGS. 1-4 comprises linkage mechanisms which include two base link-arms and seven pivot points. A thigh part C has two pivoted attachment points 1, 2 mounted on the underside of a cup-shaped structure 3, which is intended to be secured to the thigh in a conventional fashion. Two base arms A, B extend respectively from the aforesaid attachment points 1, 2 to attachment elements 4, 5 on the lower leg.

A lower-leg part D is constructed around an elongated part 6, which is constructed to carry an artificial foot 7 at its lower end and to carry a first attachment element 4 at its upper end. A second attachment element 5 is mounted on the rear side of the elongated part 6, preferably within the range of from one to three-quarters of the length of the lower leg. These attachment elements 4, 5 are intended to receive the two base arms A, B extending from the cup-shaped part 3. The attachment elements 4, 5 can also be considered as a form of moveable linkage mechanisms or rocker means.

The first attachment element 4 mounted on the upper end of the lower-leg part D can be described as a linkage mechanism having a slightly curved V-shape with three pivot points 8, 9, 10, of which the pivot point 9 is mounted or located between the other pivot points and is connected to the elongated part 6 of the lower leg. The first attachment element 4 functions as an attachment means for the base arms A, B and also as a balance-holding device whose movement is contingent on the movement of the centre of gravity of the person's body. The pivot point 9 is the point around which the first attachment element moves. The base arms A, B, which extend from the thigh part, are connected to the two pivot points 8, 10. These two pivot points 8, 10, together with the two pivot points 1, 2 at the thigh part at the ends of the first attachment element 4, can be said to form the "polycentric part" and the distance of these pivot points from one another is configured and dimensioned in accordance with the quadruple-pivot polycentric joint type.

The other attachment element 5, which is mounted approximately centrally on the elongated part 6, can be described as a linkage mechanism, rocker means or locking joint which has two pivot points 11, 12, of which the first pivot point 11 is connected with the elongated part 6 and the second pivot point 12 is connected with the rear base-part B, which extends from the thigh part C and has a curved extension on the rear side of the lower-leg part D. Arranged in the region around the second attachment element 5 is an adjustable mechanical lock-stop device 13 which has approximately the same longitudinal extension as the attachment element 5 and which is removable from the lower-leg part. The lock-stop device 13 is normally attached to the front part of the elongated part 6 and limits the movement of the attachment element 5. The lock-stop device 13 is arranged in a manner to normally provide a distinct limitation of the forward movement of the attachment element 5 and is therefore manufactured from a rigid material, preferably metal. In order to provide a certain degree of resiliency or elasticity at the movement limit position, the stop 13 may be made of a metallic material which is covered with an elastic or resilient material, or the stop and/or parts coacting therewith may alternatively be made of a material which provides a corresponding function.

The knee-joint functions in the following manner. When load is exerted on the heel, in which case the knee-joint is substantially straight, the first attachment element 4 will move clockwise around the pivot point 9 and force the second attachment element 5 to move towards the lock-stop device 13. As long as weight is exerted on the heel, it is impossible for the second attachment element 5 to open and move clockwise, even if considerable forces attempt to bend the joint. On the contrary, the locking effect is amplified instead. Because of the elasticity or resiliency of the lock-stop device, the gait of the person wearing the prosthesis will be highly similar to the gait of a normal person in setting the heel onto the ground, with subsequent locking of the knee-joint. When walking with the knee locked, the attachment element 5 may also have a given degree of resiliency against the lock-stop device 13, thereby enabling the joint to bend slightly in its locked state, which also contributes to a more natural gait.

When exerting load on the forward part of the foot, the first attachment element 4 will rock over in an anticlockwise direction. Thus, when the knee-joint is subjected to bending forces, the second attachment element 5 is able to open freely and the leg is able to swing quite freely. This takes place when it is natural to terminate or complete a walking step.

The realization that a polycentric joint can be advantageously constructed with moveable attachment elements 4, 5 on the lower leg 6 has made it possible to construct the aforedescribed knee-joint with its embodied locking function which will not prevent termination of a walking step but will assist in enabling the transition between the locking positions and the moveable positions of the knee-joint to take place automatically.

Figure 2:
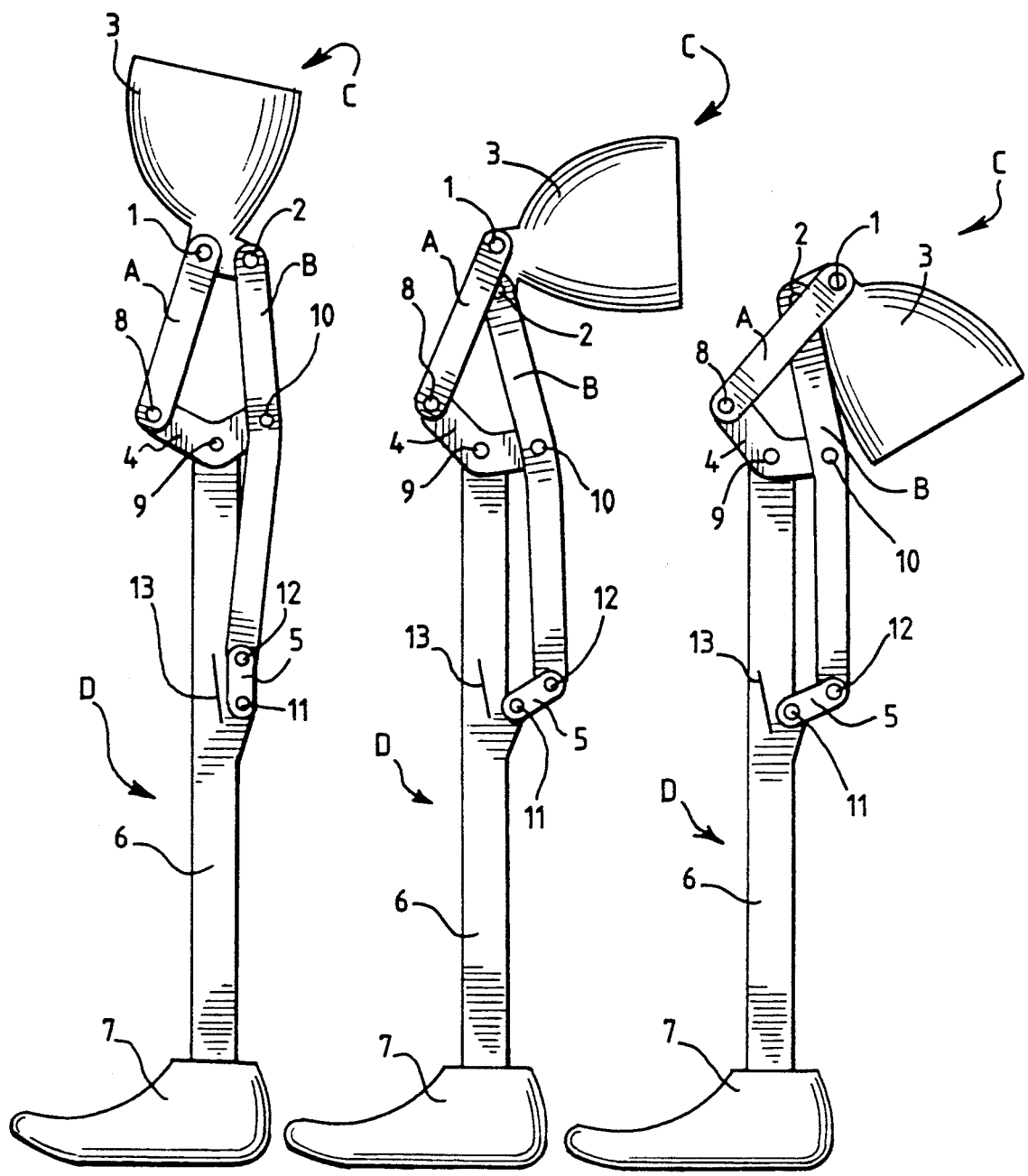
FIG. 2 illustrates different angular positions of the embodiment shown in FIG. 1 in a normal course of movement.

FIG. 2 illustrates a normal movement pattern of the knee-joint and shows the knee-joint in three different positions. In the first position, the leg is shown fully extended, whereas in the second position, the knee-joint is in a half-bent position and, finally, passes to a fully-bent position corresponding to an angle of approximately 150 degrees.

Figure 3:
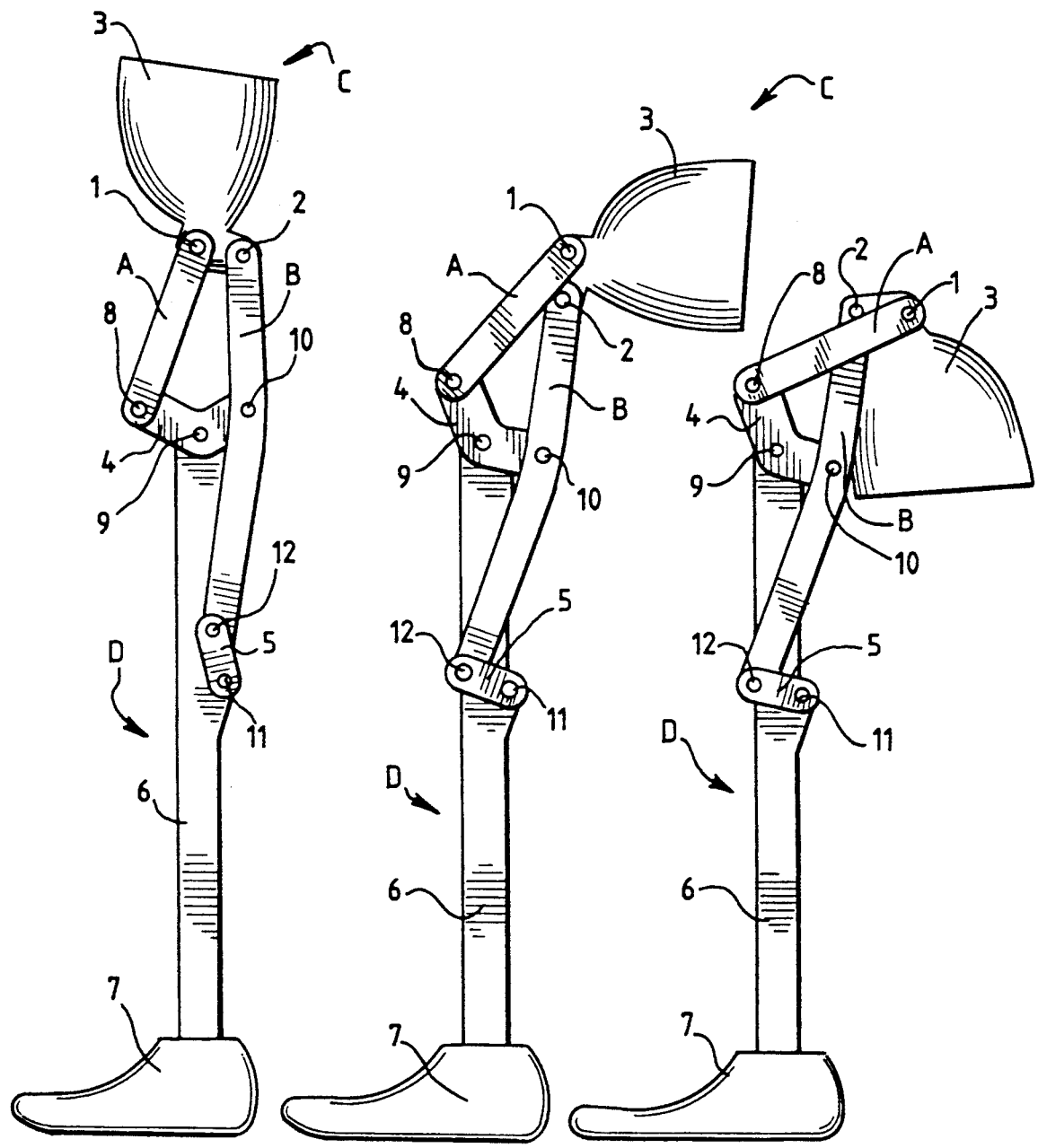
FIG. 3 illustrates another working method of the embodiment illustrated in FIG. 1, which allows different angular positions with bending up to 180 degrees.

FIG. 3 illustrates a movement pattern which includes a bend of 180 degrees. In this case, the lock-stop device is removed and the second attachment element 5 moves in an opposite direction compared with the normal movement. The drawback with this movement pattern is that when the knee-joint is in a half-bent position the lower leg will be located more forwardly than in a corresponding position with a normal movement pattern. In turn, this results in a smaller lever-arm for the thigh when walking upstairs and when cycling. This state of the knee-joint is intended, however, for use when wishing to fully bend the leg.

Figure 4:
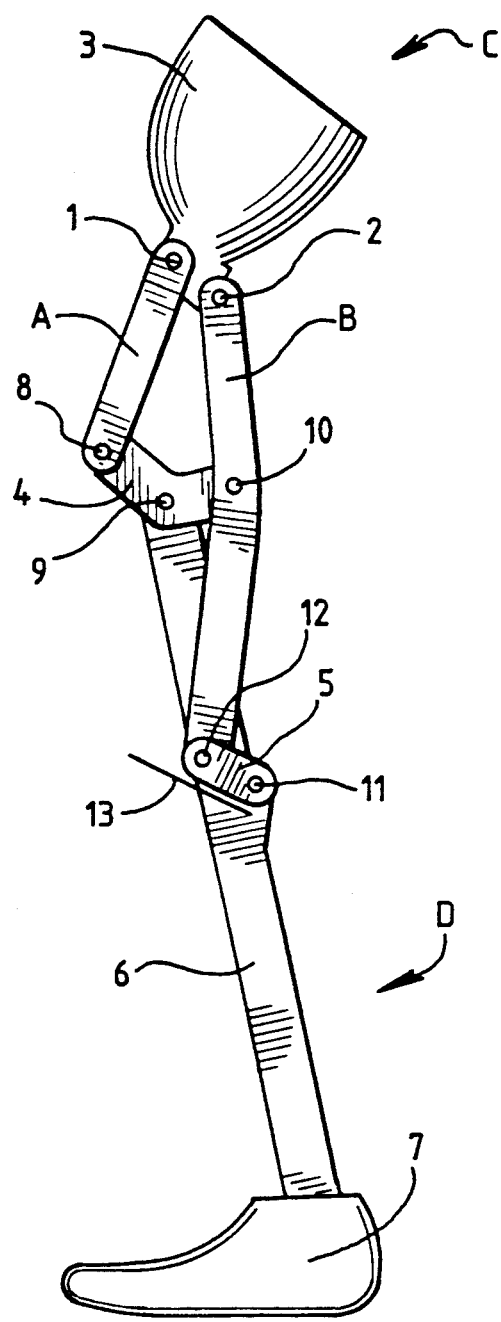
FIG. 4 illustrates the embodiment in a skiing, iceskating or dancing position.

FIG. 4 illustrates a state in which the lock-stop device 13 is displaced from the position shown in the earlier Figures. In this case, the leg can be swung freely until the user places the heel on the ground and the locking function therewith becomes operative. The advantage afforded hereby is that the user is able to participate in such activities as dancing and athletic training.

The aforedescribed knee-joint is primarily constructed for children and with view to their great need to be mobile, although the knee-joint is, of course, also well suited for adults. Because of its particular construction, the knee-joint is well suited for manufacture from some form of composite material. It is also stable and light in weight and has a wide angular range within which the knee-joint can be bent. In a normal case, the knee-joint can be bent through about 150 degrees, and in the case of a special design can be bent through about 180 degrees. It includes a simple, automatic locking function which does not prevent natural completion of a walking step and the locking effect is fully geometrical, so that in principle, there are no parts which can become worn. Furthermore, the knee-joint is locked only in the extended position of the joint and only when the heel of the foot is subjected to load.

Since the described and illustrated embodiments of the inventive knee-joint are meant solely to illustrate the inventive concept, it will be understood that the invention is not limited to these embodiments but can embrace all knee-joints which lie within the scope of the following claims.

I claim:

1. An artificial knee-joint comprising a thigh part and an elongated lower-leg part with an upper end a lower end, which parts are connected to a front linkage arm with a first end and a second end and a back linkage arm with a first end and a second end, wherein the first end of said front linkage arm is pivotally connected to said thigh part and the second end of said front linkage arm is pivotally connected to said lower-leg part, wherein the first end of said back linkage arm is pivotally connected to said thigh part and the second end of said back linkage arm is pivotally connected to said lower-leg part, characterized in that said pivotal attachment points of said second end of said front linkage arm and said second end of said back linkage arm to the lower-leg part are arranged, respectively, in a first moveable attachment element pivotally connected to the upper end of the lower-leg part and a second moveable attachment element pivotally connected to a point between the upper end and the lower end of the lower-leg part which when the knee-joint is substantially straight coact in a manner such that the knee-joint will automatically either take a substantially locked or a moveable position, depending on the direction of the load on the knee-joint, wherein the first attachment element has two or more pivot points and the second attachment element has two pivot points.

2. A knee-joint according to claim 1, characterized in that the first attachment element is pivotally connected to the second end of said front linkage arm and is pivotally connected to a point between the first end and the second end of said back linkage arm.

3. A knee-joint according to claim 1, characterized in that the back linkage arm is pivotally connected to both said first and said second attachment elements.

4. A knee-joint according to claim 1, characterized in that movement of the second attachment element is restricted by a lock-stop device.

5. A knee-joint according to claim 4 characterized in that the lock-stop device is intended to limit forward movement of both the second attachment element and of the lower part of the back linkage arm when the knee-joint is substantially straight.

6. A knee-joint according to claim 4, characterized in that the lock-stop device is positionally adjustable.

7. A knee-joint according to claim 4 characterized in that the lock-stop device in constructed in a manner to resiliently limit movement of said second attachment element and said back linkage arm.

8. An artificial knee-joint characterized by a thigh part which includes a front pivot and a back pivot and which is intended to be connected to a thigh, a lower, elongated part which includes an upper pivot at the upper end of the elongated part and a lower pivot spaced beneath the upper pivot, said elongated part forming the main part of a lower leg;

a forward base linkage arm having pivot points at the end thereof, wherein one end is pivotally connected to the front pivot of said thigh part;

a rear base linkage arm having pivot points at the ends thereof and an intermediate pivot point therebetween, wherein one end is pivotally connected to the rear pivot of said thigh part; p1 a first attachment element which includes a linkage arm having three pivot points, two at the ends thereof and a center pivot point located therebetween, wherein the center pivot point is joined to the upper pivot point of said elongated part and the two remaining pivot points are moveably connected to the lower pivot point of the front base linkage arm and to the intermediate pivot point of the rear base linkage arm, respectively;

a second attachment element which includes a linkage arm having pivot points at the ends thereof, wherein one end is pivotally connected to the lower pivot point of the elongated part and the other end is pivotally connected to the lower pivot point of the rear base linkage arm;

a mechanical stop means for limiting forward movement of the lower pivot point of the rear base linkage arm in relation to the elongated part, wherein the various parts are so dimensioned and arranged that the joint is locked by virtue of the fact that the lower pivot point is pressed harder against the stop means with increasing pressure when the weight rests on the back of the artificial knee-joint, whereas the lower pivot point leaves its abutment with the stop means, so as to enable the knee-joint to bend when the weight is transferred over to the front of the artificial knee-joint.

* * * * *